United States Patent [19]

Thompson et al.

[11] 4,260,817
[45] Apr. 7, 1981

[54] PROCESS FOR THE PURIFICATION OF TEREPHTHALIC ACID

[75] Inventors: David T. Thompson, Whitchurch Hill; Alfred J. Bird, Hounslow; Edward J. Pearson, Caversham Park Village, all of England

[73] Assignee: Johnson, Matthey & Co., Limited, London, England

[21] Appl. No.: 952,140

[22] Filed: Oct. 17, 1978

Related U.S. Application Data

[63] Continuation of Ser. No. 774,042, Mar. 3, 1977, abandoned.

[30] Foreign Application Priority Data

Mar. 5, 1976 [GB] United Kingdom ............... 8932/76

[51] Int. Cl.$^3$ ............................................. C07C 51/42
[52] U.S. Cl. ............................................................ 562/487
[58] Field of Search ........................ 562/487; 260/525

[56] References Cited

U.S. PATENT DOCUMENTS

| | | | |
|---|---|---|---|
| 3,456,001 | 7/1969 | Olsen | 562/487 |
| 3,546,285 | 12/1970 | Witt | 562/487 |
| 3,607,921 | 9/1971 | Stancell | 562/487 |
| 3,637,831 | 1/1972 | Remsberg | 562/487 |

*Primary Examiner*—Alan Siegel
*Attorney, Agent, or Firm*—Cushman, Darby & Cushman

[57] ABSTRACT

This invention relates to catalysis for example, the catalytic hydrogenation of impurities in terephthalic acid to yield terephthalic acid of sufficient purity for use in the production of polyester fibres. In more detail, the invention comprises the step of treating a solution of terephthalic acid with hydrogen gas in the presence of a catalyst comprising two or more of the metals platinum, palladium, rhodium, ruthenium, osmium and irridium.

9 Claims, No Drawings

PROCESS FOR THE PURIFICATION OF TEREPHTHALIC ACID

This is a continuation of application Ser. No. 774,042, filed Mar. 3, 1977, now abandoned.

This invention is concerned with improvements in and relating to catalysis. More particularly, the invention provides a process for the catalytic hydrogenation of impurities in terephthalic acid so as to yield terephthalic acid of sufficient purity for use in the production of polyester fibres by a process which includes the direct esterification of the acid with a glycol.

In the manufacture of polyester fibres, such as Terylene (Registered Trade Mark) fibres by a process of the type just referred to, terephthalic acid is typically esterified with ethylene glycol to yield bis-hydroxy-ethylene-terephthalate (bisHET) as follows:

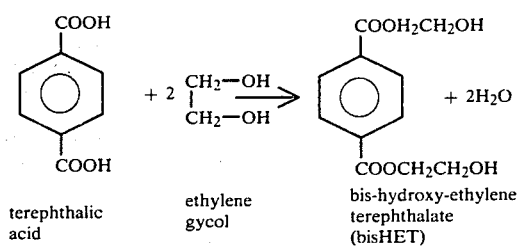

The resulting bisHet is then converted to polyethylene terephthalate by a process of polycondensation:

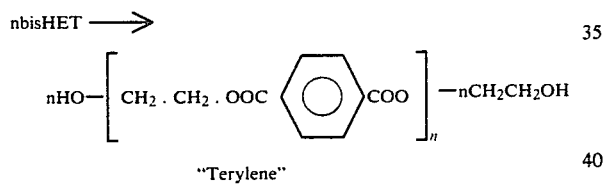

The process as just outlined has the merits of simplicity and economy but it does require the use of terephthalic acid of very high purity. Terephthalic acid may be prepared by oxidising p-xylene with permanganate or by a catalytic oxidation process employing bromine as the catalyst. None of the available methods of producing the acid by the oxidation of p-xylene, however, will normally yield an acid of sufficient purity for direct esterification in the production of polyester fibres. The principal impurity in terephthalic acid made by this oxidation route is 4-carboxybenzaldehyde, an intermediate product in the oxidation of p-xylene to terephthalic acid, in which one of the methyl groups is fully oxidised to a carboxylic acid group but in which the other group is oxidised, only partially, to an aldehyde group, as follows:

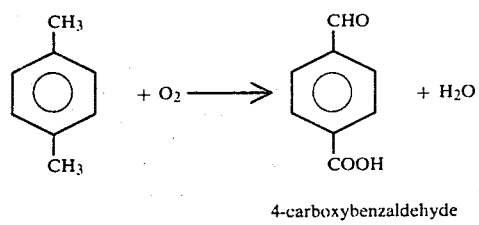

Two other impurities which may exist in the terephthalic acid are:

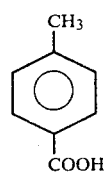

P-toluic acid, and

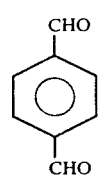

terephthaldehyde

These are again intermediate products in the oxidation of p-xylene.

The p-toluic acid is very much more soluble in water than terephthalic acid and therefore may easily be removed therefrom.

The two aldehyde species, 4-carboxybenzaldehyde and terephthaldehyde, on the other hand, both of which adversely affect the polycondensation stage and both of which vitiate the quality of any resulting polyester fibre and give rise to a rapid yellowing of fabrics made therefrom, cannot be removed in the same way. They may, however, very conveniently be removed by hydrogenating them respectively to p-toluic acid and p-xylene as shown:

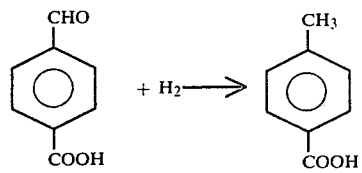

4-carboxybenzaldehyde    p-toluic acid

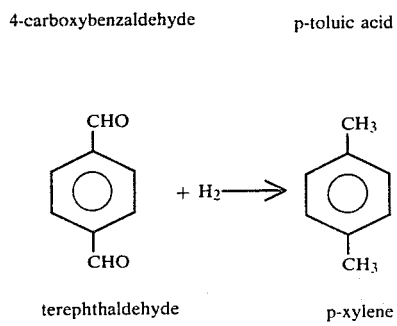

terephthaldehyde    p-xylene and it is an object of the present invention to provide a catalytic process whereby this hydrogenation may conveniently and expeditiously be effected.

The advantages of hydrogenating the aldehyde impurities in impure terephthalic acid, and, especially the impurity 4-carboxybenzaldehyde, have previously been recognised and, indeed, a 0.5 wt. % palladium on charcoal catalyst is used for the purpose.

We have now discovered, however, that the reduction of 4-carboxybenzaldehyde and other aldehydes takes place in two stages and that when the conventional palladium on charcoal catalyst is used, the rate of reaction during the second stage is very significantly lower than during the first stage. During the first stage at least some of the aldehyde (CHO) groups are reduced to alcohol (CH$_2$OH) groups whilst, during the second stage, at least some of these alcohol groups are further reduced to methyl (CH$_3$) groups and the saturated product appears. The present invention provides a catalytic process for the purification of terephthalic acid by the hydrogenation of aldehyde impurities therein whereby the second stage of the hydrogenation process previously referred to, during which the alcohol groups are reduced to methyl groups, is significantly speeded up as compared with the corresponding rate of reaction when a conventional palladium on charcoal catalyst is used, without, at the same time, markedly affecting the rate of reaction during the first stage.

The catalytic process as just described will, throughout the remainder of the specification, be referred to as a "catalytic process of the type herein described". It will, therefore, be appreciated that a catalytic process of the type herein described yields terephthalic acid which is sufficiently pure to permit its direct esterification with glycol in the manufacture of polyester fibre.

According to the invention, a catalytic process of the type herein described includes the step of treating a solution of terephthalic acid with hydrogen gas in the presence of a catalyst comprising two or more of the metals platinum, palladium, rhodium, ruthenium, osmium and iridium.

In addition, the catalyst may include one or more of the metals iron, nickel, cobalt, chromium, manganese and uranium.

Preferably:

(a) the catalyst used in a catalytic process of the type herein described comprises one or more of the pairs of metals:
palladium : ruthenium
palladium : osmium
palladium : iridium
palladium : rhodium
palladium : platinum
platinum : rhodium
palladium : iron
palladium : nickel
palladium : cobalt
palladium : chromium
palladium : manganese
palladium : uranium (b) the metals of the catalyst may be alloyed together although they may also be more loosely associated than in an alloy. They may, for example, be in the form of a simple mixture or of an intimate, essentially homogeneous, mixture which is other than a mere physical admixture.

(c) the catalyst metal is deposited on or associated with a support.

(d) the support is in the form of carbon particles or granules, within the size range of 4 to 8 BS Mesh.

(e) a catalytic process of the type herein described is carried out at elevated temperature and pressure, for example, at 280° C. and 1,500 p.s.i.

Although reference has been made to a support in the form of particles or granules, the support may also be in the form of a carbon, ceramic or metal honeycomb structure. In the case of a non-carbon structure, the structure is preferably coated with a carbon or a carbonised material.

One way in which the invention may be put into effect is to allow an aqueous solution of impure terephthalic acid to flow downwards through a catalyst packed column with hydrogen gas flowing upwards through the column. The process is typically conducted at a temperature of 300° C. and at a pressure of about 1,500 p.s.i., the purified terephthalic acid is recovered from the treated solution by crystallisation and filtration and the filtrate then recycled. The p-toluic acid and p-xylene it contains is thus subjected to the hydrogenation process in the column together with fresh terephthalic acid solution introduced into the column.

We have obtained very promising results using a bimetallic catalyst containing 0.4 wt. % palladium and 0.1 wt. % platinum on 4 BS Mesh carbon particles. Typically, we have found that the rate of hydrogen uptake per unit weight of catalyst with the palladium/platinum catalyst just referred to is 20% higher than with a catalyst consisting of 0.5 wt. % palladium on 4 BS Mesh carbon particles.

What we claim is:

1. In a catalytic process for purifying terephthalic acid prepared by catalytic oxidation of p-xylene and which includes 4-carboxybenzaldehyde and terephthaldehyde as aldehydic impurities, said purification process involving catalytically hydrogenating the impure terephthalic acid to convert 4-carboxybenzaldehyde and terephthaldehyde therein to p-toluic acid and p-xylene, respectively, by a reaction mechanism which involves first converting the aldehyde (CHO) groups to alcohol (CH$_2$OH) groups and then converting the latter to methyl (CH$_3$) groups, the improvement comprising carrying out the hydrogenation of the impure terephthalic acid by contacting an aqueous solution of the impure acid with hydrogen gas, as the sole gaseous reactant, in the presence of a catalyst selected from one of the following metal combinations:
palladium : ruthenium
palladium : osmium
palladium : iridium
palladium : rhodium
palladium : platinum
platinum : rhodium
palladium : iron
palladium : nickel
palladium : cobalt
palladium : chromium
palladium : manganese
palladium : uranium,
said catalyst functioning to improve the speed at which the alcohol groups are converted to methyl groups without markedly affecting the speed of the initial conversion of aldehyde groups to alcohol groups.

2. A process according to claim 1 wherein the metals of the catalyst constitute an alloy.

3. A process according to claim 1 wherein the metals of the catalyst are in the form of a mixture.

4. A process according to claim 3 wherein the catalyst metal is deposited on a support.

5. A process according to claim 4 wherein the support is in the form of carbon granules within the range 4 to 8 BS mesh.

6. A process according to claim 1 wherein the treatment of the said solution is carried out at elevated temperature and pressure.

7. A process according to claim 6 wherein the temperature and pressure are 280° C. and 1,500 p.s.i. respectively.

8. A process according to claim 1 wherein the catalyst comprises 0.4 wt % palladium and 0.1 wt % platinum supported on 4 BS mesh carbon particles.

9. The process of claim 1 wherein after said contacting step, the terephthalic acid is crystallized and filtered from the remaining solution and the filtrate is recycled to the catalytic hydrogenation step for hydrogenation with the impure terephthalic acid.

* * * * *